US006995154B2

(12) United States Patent
LaVoie et al.

(10) Patent No.: US 6,995,154 B2
(45) Date of Patent: Feb. 7, 2006

(54) HETEROCYCLIC TOPOISOMERASE POISONS

(75) Inventors: Edmond J. LaVoie, Princeton Junction, NJ (US); Jung Sun Kim, Pusan (KR); Leroy Fong Liu, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/690,800

(22) Filed: Oct. 21, 2003

(65) Prior Publication Data

US 2004/0082637 A1 Apr. 29, 2004

Related U.S. Application Data

(60) Division of application No. 09/869,141, filed on Jun. 13, 2001, now Pat. No. 6,667,302, which is a continuation of application No. PCT/US98/27822, filed on Dec. 30, 1998.

(60) Provisional application No. 60/070,287, filed on Dec. 31, 1997.

(51) Int. Cl.
*A61K 31/55* (2006.01)
*A61K 31/495* (2006.01)
*A61K 31/50* (2006.01)
*A01N 43/00* (2006.01)
*A01N 43/58* (2006.01)

(52) U.S. Cl. .................. 514/211.09; 514/212.07; 514/221; 514/222.6; 514/243; 514/249; 514/299; 514/359; 514/367; 514/375; 514/307; 514/312; 514/314; 514/230.05; 514/248; 514/213.01; 514/259.5; 514/394; 514/301; 514/302; 544/353; 544/354; 544/50; 544/51; 544/105; 544/235; 544/284; 540/567; 540/593; 540/468; 540/569; 548/305.1; 548/305.4

(58) Field of Classification Search ........... 514/211.09, 514/212.07, 221, 222.6, 243, 249, 299, 359, 514/367, 375, 307, 312, 314, 230.05, 248, 514/259.5, 213.01; 540/567, 593, 468, 569; 548/305.4, 305.1; 544/353, 354, 50, 51, 544/105, 235, 284
See application file for complete search history.

(56) References Cited

U.S. PATENT DOCUMENTS

| | | | |
|---|---|---|---|
| 26,065 A | 11/1859 | Marvel et al. ............... 260/47 |
| 2,985,661 A | 5/1961 | Hien et al. ................. 260/309 |
| 3,449,330 A | 6/1969 | Guglielmetti et al. ....... 260/240 |
| 3,538,097 A | 11/1970 | Lowe et al. ............... 260/268 |
| 5,106,863 A | 4/1992 | Hajos et al. ............... 514/395 |
| 5,112,532 A | 5/1992 | Ninomiya et al. .......... 252/587 |
| 5,767,142 A | 6/1998 | La Voie et al. ............ 514/394 |
| 5,770,617 A | 6/1998 | LaVoie et al. ............. 514/394 |
| 5,807,874 A | 9/1998 | LaVoie et al. ............. 514/338 |

FOREIGN PATENT DOCUMENTS

| | | |
|---|---|---|
| RU | 1530628 | 12/1989 |
| WO | WO-96/36612 | 11/1996 |
| WO | WO-98/31673 | 7/1998 |

OTHER PUBLICATIONS

Carter, Stephen K., M.D. et al.; Chemotherapy of Cancer, Second Edition, (1981); A Wiley & Sons, New York, New York; pp 362-365.*

Dancey et al. "Current perspectives on camptothecins in cancer treatment" 1996, British Journal of Cancer, 74, 327-38.*

Rangarajan et al. "2"-substituted 5-Phenylterbenzimidazoles as Topoisomerase I Poisons" 2000, Bioorganic & Medicinal Chemistry, 8, 1371-82.*

Loewe et al. "Basic substituted 2,6-bisbenzimidazole derivatives, a novel series of substances with chemotherapeutic activity" 1974, Arzneimittel-Forschchung, 24(12), 1927-33.*

International PCT Search Report for PCT/US 98/01005, (Jun. 22, 1998),5 pgs.

Bathini, Yadagiri, et al., "Convenient Routes to Substituted Benzimidazoles and Imidazolo[4,5-b]pyridines Using Nitrobenzene as Oxidant", *Synthetic Communications*, 20 (7), (1990),pp. 955-963.

(Continued)

*Primary Examiner*—Sreeni Padmanabhan
*Assistant Examiner*—Gregory W. Mitchell
(74) *Attorney, Agent, or Firm*—Viksnins Harris & Podys PLLP

(57) ABSTRACT

The invention provides compounds of formula I:

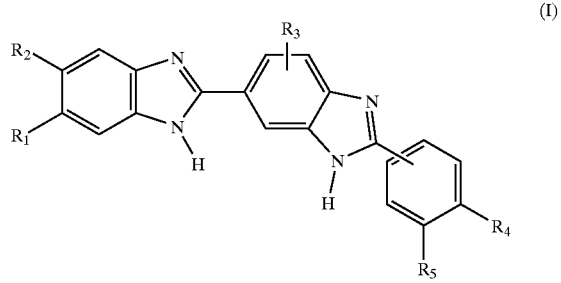

wherein $R_1$ to $R_5$ have any of the values defined in the specification, as well as pharmaceutically acceptable salts of the compounds, pharmaceutical compositions comprising the compounds, and methods of using the compounds, compositions, or salts to treat cancer. In embodiments, $R_4$ and $R_5$ taken together can be a 3, 4, or 5 membered saturated or unsaturated chain comprising members selected from the group consisting of non-peroxide oxygen, sulfur, N(X), and carbon, optionally substituted by oxo; wherein each X is independently absent or is H, O, ($C_1$–$C_4$)alkyl, phenyl or benzyl; and wherein at least one of the chain members is an N—H group.

28 Claims, 2 Drawing Sheets

OTHER PUBLICATIONS

Chen, Allan Y., et al., "A New Mammalian DNA Topoismerase I Poison Hoechst 33342: Cytoxicity and Drug Resistance in Human Cell Cultures", *Cancer Research, 53* (6), (Mar. 15, 1993),pp. 1332-1337.

Chen, Allan Y., et al., "DNA Minor Groove-Binding Ligands: A Different Class of Mammalian DNA Topoisomerase I Inhibitors", *Proc. Natl. Acad. Sci., USA, 90*, (Sep. 1993),pp. 8131-8135.

Chen, Allan Y., et al., "DNA Topoisomerases: Essential Enzymes and Lethal Targets", *Annu. Rev. Pharmacol. Toxicol., 34*, (1994),pp. 191-218.

Goldman, Gustavo H., et al., "Differential poisoning of humand and aspergilus nidulans DNA topoisomerase I by Bi- and Terbenzimidazoles", *Biochemistry, 36* (21), (1997), pp. 6488-6494.

Kim, J.S., et al., "Influence of steric factors on topoismerase I inhibition and cytotoxicity of bisbenzimidazoles related to Hoechst 33342", *Proceedings of the 86th Annual Meeting of the American Association for Cancer Research, 36*, Abstract No. 2689, Toronto, Ontario, Canada,(Mar. 1995), p. 451.

Kim, J. S., et al., "Influence of steric factors on topoisomerase I inhibition and cytotoxicity of bisbenzimidazoles related to Hoechst 33342", *Abstract 7—Proceedings of the 3rd Annual Scientific Retreat of the Cancer Institute of New Jersey*, Princeton Marrtott Forrestal Village,(1995),p. 28.

Kim, Jung S., et al., "Quantitative structure-activity relationships on 5-substituted terbenzimidazoles as topoisomerase I poisons and antitumor agents", *Bioorg. Med. Chem., 6* (2), (1998),pp. 163-172.

Kim, J. S., et al., "Steric factors associated with the topoisomerase I inhibition and cytotoxicity of substituted bisbenzimidazoles", *Abstract 10-Proceedings of the American Association of Pharmaceutical Scientists Eastern Regional Meeting*, (1995),p. 27.

Kim, Jung S., et al., "Structure-activity Relationships of Benzimidazoles and Related Heterocycles as Topoisomerase I Poisons", *Bioorganic & Med. Chem., 4*, (1996),pp. 621-630.

Kim, Jung S., et al., "Substituted 2,5'-Bi-1H-benzimidazoles: Topoisomerase I Inhibition and Cytotoxicity", *J. Med. Chem., 39*, (1996),pp. 992-998.

Kim, Jung S., et al., "Terbenzimidazoles: influence of 2"-, 4-, and 5- substituents on cytotoxicity and relative potency as topoisomerase I poisons", *J. Med. Chem., 40*, (1997),pp. 2818-2824.

LaVoie, E. J. et al., "Structure-activity studies related to minor groove-binding ligands which inhibit mammalian DNA topoisomerase I", *Abstract 1—Proceedings of the 85th Annual Meeting of American Association for Cancer Research*, San Francisco, CA,(Apr. 1994),p. 2699.

Loewe, H., et al., "Basic substituted 2, 6-bisbenzimidazole derivatives, a novel series of substances with chemotherapeutic activity", *Chemical Abstracts, 82* (17), Abstract No. 112032,(Apr. 28, 1975),1 p.

Pilch, Daniel S., et al., "A terbenzimidazole that preferentially binds and conformationally alters structurally distinct DNA duplex domains: a potential mechanism for topoisomerase I poisoning", *Proc. Nat'l. Acad. Sci., USA, 94*, (Dec. 1997),pp. 13565-13570.

Pilch, Daniel S., et al., "Biophysical Characterization of a Cytotoxic, Topoisomerase I Poison", *Abstract 8—Proceedings of the 3rd Annual Scientific Retreat of the Cancer Institute of New Jersey*, Princeton Marriott Forrestal Village, Princeton, NJ,(Jun. 1, 1995),p. 3.

Pilch, Daniel S., et al., "Characterizing the DNA binding modes of a topoisomerase I-poisoning terbenzimidazole: evidence for both intercalative and minor groove binding properties", *Drug Design and Discovery, 13*, (1996),pp. 115-133.

Porai-Koshits, B.A., et al., "Imidazole derivatives. Synthesis of some polybenzimidazoles", *Zhur. Obshchei Khim, 23*, As related in Chemical Abstracts, 48 (1954) Col. 4523,(1953), pp. 835-841.

Singh, Malvinder P., et al., "Synthesis and Sequence-Specific DNA Binding of a Topoisomerase Inhibitory Analog of Hoechst 33258 Designed for Altered Base and Sequence Recognition", *Chem. Res. Toxicol., 5*, (1992),pp. 597-607.

Sun, et al., *Chemical Abstracts, 123* (15), Abstract No. 198740r, (1995), 1 p.

Sun, Qun, et al., "Structure activity of novel topoisomerase I inhibitors related to Hoechst 33342", *Abstract 6—Proceedings of the American Association of Pharmaceutical Scientists Eastern Regional Meeting*, Hyatt Regency Hotel, New Brunswick, NJ,(Jun. 5-6, 1995),p. 25.

Sun, Qun, et al., "Structure Activity of Topoisomerase I Poisons related to Hoechst 33342", *Bioorganic & Medicinal Chemistry Letters*, vol. 4, No. 24 vol. 4, No. 24,(1994),pp. 2871-2876.

Sun, Qun, et al., "Structure-activity studies related to minor groove-binding ligands which inhibit mammalian DNA topoisomerase I", *Cancer Institute of New Jersey's First Annual Scientific Retreat, Abstract 2*, Princeton Marriott Forrestal Village, Princeton, NJ,(Jun. 7, 1994),p. 66.

Sun, Sun, et al., "Synthesis and Evaluation of Terbenzimidazoles as Topoisomerase I Inhibitors", *J. Med. Chem, 38*, (1995),pp. 3638-3644.

Sun, Qun, et al., "Synthesis and Evaluation of Terbenzimidazoles as Topoisomerase I Inhibitors", *Chemical Abstracts, 123* (15), Abstract No. 198740r,(1995),p. 1241.

Sun, Q., et al., "Synthesis and Pharmacological Evaluation of a Series of Novel DNA Topoisomerase I Inhibitors as Antitumor Agents", *Scientific Proceedings of 86th Annual Meeting of the American Association for Cancer Research, Abstract 3*, Toronto, Canada, (Mar. 18-22, 1995),1 p.

Sun, Qun, et al., "Synthesis and pharmacological evaluation of a series of novel DNA topoisomerase I inhibitors as antitumor agents", *Proceedings of the 86th Annual Meeting of the American Association for Cancer Research*, Toronto, Ontario, Canada,(1995),p. 2688.

Sun, Qun, et al., "Synthesis and pharmacological evaluation of a series of novel DNA topoisomerase I inhibitors as antitumor agents", *Abstract 5—Proceedings of the 3rd Annual Scientific Retreat of the Cancer Institute of New Jersey*, Princeton Marriott Forrestal Village, Princeton, NJ,(1995),p. 27.

Sun, Qun, et al., "Synthesis of Benzimidazo[2,1-a]isoquinolines and 5,6-Dihydrobenzimidazo[2,1-a]isoquinolines",*Syn. Lett., submitted*, Paper No. 7,(1995),6 p.

Vinogradov, A. E., et al., "Some properties of new DNA specific bisbenzimidazole fluorochromes without a piperazine ring", *Biotechnic & Histochemistry, 38* (5), (1993),pp. 265-269.

Yadagiri, Bathini, et al., "Convenient Routes to Substituted Benzimidazoles and Imidazolo[4,5-b]Pyridines Using Nitrobenzene as Oxidant", *Synthetic Communications, 20* (7), (1990),pp. 955-963.

* cited by examiner

HETEROCYCLIC TOPOISOMERASE POISONS

CROSS-REFERENCE TO RELATED APPLICATIONS

This application is a divisional application of U.S. patent application Ser. No. 09/869,141, issued as U.S. Pat. No. 6,667,302, filed on Jun. 13, 2001, entitled "Heterocyclic Topoisomerase Poisons", which is a continuation of PCT Application No. 98/27822, filed on Dec. 30, 1998, entitled "Heterocyclic Topoisomerase Poisons", which claims priority to U.S. Provisional Application 60/070,287, filed on Dec. 31, 1997, entitled "Heterocyclic Topoisomerase Poisons".

BACKGROUND OF THE INVENTION

DNA-topoisomerases are enzymes present in the nuclei of cells where they catalyze the breaking and rejoining of DNA strands, controlling the topological state of DNA. Recent studies also suggest that topoisomerases are involved in regulating template supercoiling during RNA transcription. There are two major classes of mammalian topoisomerases. DNA-topoisomerase-I catalyzes changes in the topological state of duplex DNA by performing transient single-strand breakage-union cycles. In contrast, mammalian topoisomerase II alters the topology of DNA by causing a transient enzyme bridged double-strand break, followed by strand passing and resealing. Mammalian topoisomerase II has been further classified as Type II α and Type II β. The antitumor activity associated with agents which are topoisomerase poisons is associated with their ability to stabilize the enzyme-DNA cleavable complex. This drug-induced stabilization of the enzyme-DNA cleavable complex effectively converts the enzyme into a cellular poison.

Several antitumor agents in clinical use have potent activity as mammalian topoisomerase II poisons. These include adriamycin, actinomycin D, daunomycin, VP-16, and VM-26 (teniposide or epipodophyllotoxin).

In contrast to the number of clinical and experimental drugs which act as topoisomerase II poisons, there are currently only a limited number of agents which have been identified as topoisomerase I poisons. Camptothecin and its structurally-related analogs are among the most extensively studied topoisomerase I poisons. Recently, bi- and terbenzimidazoles (Chen et al., Cancer Res. 1993, 53, 1332–1335; Sun et al., J. Med. Chem. 1995, 38, 3638–3644; Kim et al., J. Med. Chem. 1996, 39, 992–998), certain benzo[c]phenanthridine and protoberberine alkaloids and their synthetic analogs (Makhey et al., Med. Chem. Res. 1995, 5, 1–12; Janin et al., J. Med. Chem 1975, 18, 708–713; Makhey et al., Bioorg. & Med. Chem. 1996, 4, 781–791), as well as the fungal metabolites, bulgarein (Fujii et al., J. Biol. Chem. 1993, 268, 13160–13165) and saintopin (Yamashita et al., Biochemistry 1991, 30, 5838–5845) and indolocarbazoles (Yamashita et al., Biochemistry 1992, 31, 12069–12075) have been identified as topoisomerase I poisons.

Presently, a need exists for novel anti-cancer agents, for anti-cancer agents that exhibit improved activity, and for anti-cancer agents that exhibit fewer side-effects or improved selectivity compared to existing agents.

SUMMARY OF THE INVENTION

The present invention provides compounds that exhibit inhibitory activity against topoisomerase I, and compounds that are effective cytotoxic agents against cancer cells, including drug-resistant cancer cells. Accordingly there is provided a compound of the invention which is a compound of formula I:

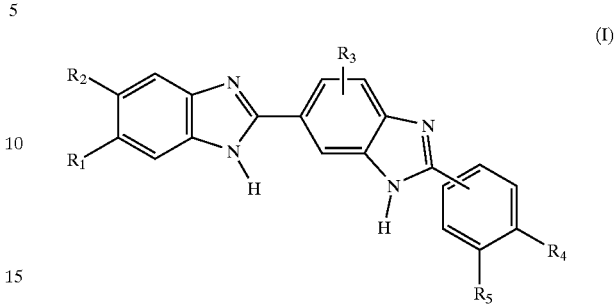

(I)

wherein
$R_1$ and $R_2$ are each independently hydrogen, $(C_1-C_6)$ alkyl, $(C_3-C_6)$cycloalkyl, $(C_1-C_6)$alkoxy, nitro, hydroxy, halo$(C_1-C_6)$alkyl, trifluoromethoxy, halo, $(C_3-C_6)$cycloalkyl$(C_1-C_6)$alkyl, $(C_1-C_6)$alkanoyl, hydroxy$(C_1-C_6)$ alkyl, $(C_1-C_6)$alkoxycarbonyl, $(C_1-C_6)$alkylthio, $(C_2-C_6)$ alkanoyloxy, aryl or heteroaryl; or $R_1$ and $R_2$ taken together are methylenedioxy; or $R_1$ and $R_2$ taken together are benzo; wherein any aryl, heteroaryl, or benzo may optionally be substituted by 1, 2, or 3 substituents independently selected from the group consisting of $(C_1-C_6)$alkyl, $(C_3-C_6)$cycloalkyl, $(C_1-C_6)$alkoxy, nitro, hydroxy, halo$(C_1-C_6)$alkyl, trifluoromethoxy, $(C_3-C_6)$cycloalkyl$(C_1-C_6)$alkyl, $(C_1-C_6)$ alkanoyl, hydroxy$(C_1-C_6)$alkyl, $(C_1-C_6)$alkoxycarbonyl, $(C_1-C_6)$alkylthio, $(C_2-C_6)$alkanoyloxy, and halo;
$R_3$ is hydrogen, $(C_1-C_6)$alkyl, $(C_3-C_6)$cycloalkyl, $(C_1-C_6)$alkoxy, nitro, hydroxy, halo$(C_1-C_6)$alkyl, trifluoromethoxy, $(C_3-C_6)$cycloalkyl$(C_1-C_6)$alkyl, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, or halo; and
$R_4$ and $R_5$ taken together are a 3, 4, or 5 membered saturated or unsaturated chain comprising members selected from the group consisting of non-peroxide oxygen, sulfur, N(X), and carbon, optionally substituted by oxo; wherein each X is independently absent or is H, O $(C_1-C_4)$alkyl, phenyl or benzyl; and wherein at least one (e.g. 1 or 2) of said chain members is an N—H group;
or a pharmaceutically acceptable salt thereof;
provided $R_4$ and $R_5$ taken together are not —N(H)—C(H)=N—.

Preferably, any carbon of $R_4$ and $R_5$ is saturated (—CH$_2$—) or unsaturated (=CH—).

The invention also provides a pharmaceutical composition comprising a compound of formula I, or a pharmaceutically acceptable salt thereof, in combination with a pharmaceutically acceptable diluent or carrier.

The invention also provides a therapeutic method comprising inhibiting cancer cells by administering to a mammal (e.g. a human) in need of such therapy, an amount of a compound of formula I, or a pharmaceutically acceptable salt thereof, effective to inhibit said cancer cells.

The invention also provides a method comprising inhibiting cancer cells by contacting said cancer cells in vitro or in vivo with an amount of a compound of formula I, or a pharmaceutically acceptable salt thereof, effective to inhibit said cancer cells, i.e. to inhibit their activity, such as their ability to divide, migrate, or proliferate.

The invention also provides a compound of formula I for use in medical therapy (preferably for use in treating cancer, e.g. solid tumors), as well as the use of a compound of formula I for the manufacture of a medicament useful for the treatment of cancer, e.g. solid tumors.

The invention also provides processes and novel intermediates disclosed herein which are useful for preparing compounds of the invention. Some of the compounds of formula I are useful to prepare other compounds of formula I.

DETAILED DESCRIPTION

Figure 1:
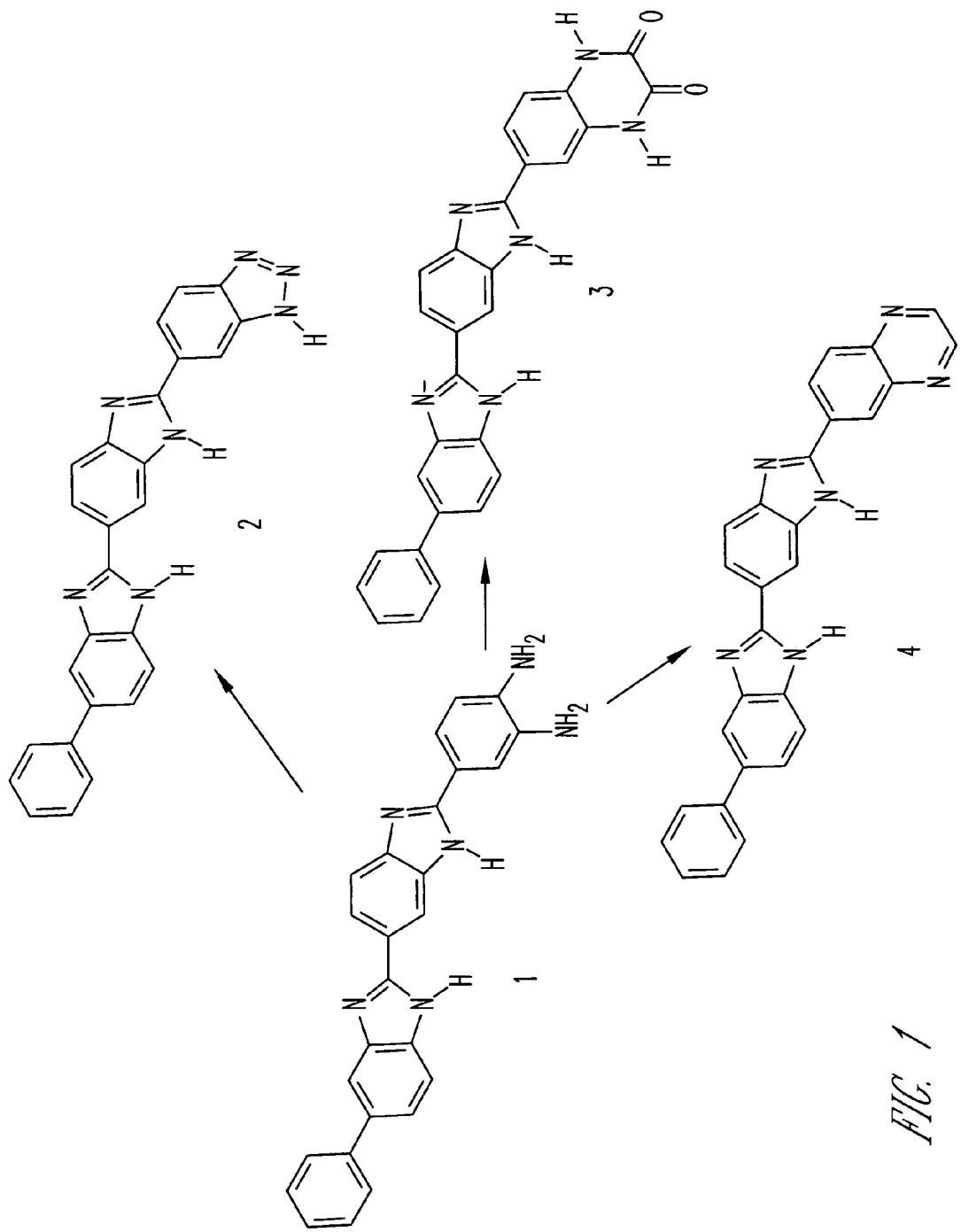
FIG. 1 Illustrates the synthesis of compounds of the invention (2 and 3) and the synthesis of compound 4.
Figure 2:
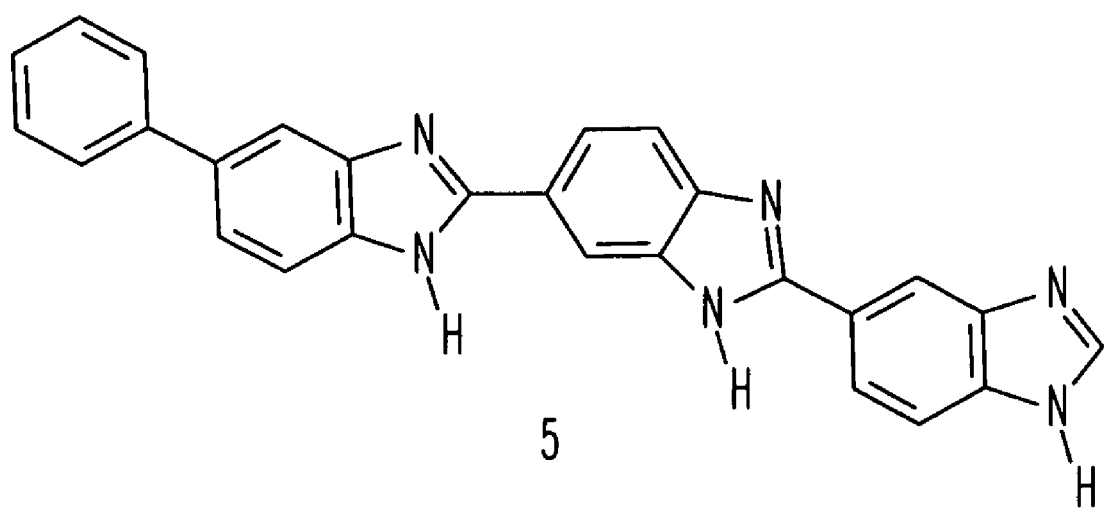
FIG. 2 Shows the structure of compound 5.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(Y) wherein Y is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine topoisomerase poisoning activity or cytotoxic activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$ is hydrogen, halo, aryl or heteroaryl; wherein any aryl or heteroaryl may optionally be substituted by 1, 2, or 3 substituents independently selected from the group consisting of $(C_1-C_6)$alkyl, $(C_3-C_6)$cycloalkyl, $(C_1-C_6)$alkoxy, nitro, hydroxy, halo$(C_1-C_6)$alkyl, trifluoromethoxy, and halo.

A specific value for $R_2$ is hydrogen, halo, aryl or heteroaryl; wherein any aryl or heteroaryl may optionally be substituted by 1, 2, or 3 substituents independently selected from the group consisting of $(C_1-C_6)$alkyl, $(C_3-C_6)$cycloalkyl, $(C_1-C_6)$alkoxy, nitro, hydroxy, halo$(C_1-C_6)$alkyl, trifluoromethoxy, $(C_3-C_6)$cycloalkyl$(C_1-C_6)$alkyl, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, and halo.

Specifically, $R_1$ and $R_2$ taken together can be methylenedioxy.

Specifically, $R_1$ and $R_2$ taken together can be benzo, which benzo may optionally be substituted by 1, 2, or 3 substituents independently selected from the group consisting of $(C_1-C_6)$alkyl, $(C_3-C_6)$cycloalkyl, $(C_1-C_6)$alkoxy, nitro, hydroxy, halo$(C_1-C_6)$alkyl, trifluoromethoxy, $(C_3-C_6)$cycloalkyl$(C_1-C_6)$alkyl, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, and halo.

A specific value for $R_3$ is hydrogen. Another specific value for $R_3$ is $(C_1-C_6)$alkoxy, nitro, hydroxy, halo$(C_1-C_6)$alkyl, trifluoromethoxy, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, or halo.

Specifically, $R_4$ and $R_5$ taken together can be —N(H)—N=N—, —N(H)—N(H)—CH$_2$—, —N(H)—N(H)—CH$_2$—CH$_2$—, —N(H)—CH$_2$—N(H)—, —N(H)—CH=CH—, —N(H)—CH$_2$—CH$_2$—, —N(H)—CH$_2$—CH$_2$—CH$_2$—, —N(H)—CH$_2$—CH$_2$—CH$_2$—CH$_2$—, —N(H)—CH$_2$—CH$_2$—N(H)—, —N(H)—CH$_2$—CH$_2$—O—, —N(H)—CH$_2$—CH$_2$—S—, —N(H)—CH$_2$—CH$_2$—CH$_2$—N(H)—, —N(H)—CH$_2$—CH$_2$—CH$_2$—O—, —N(H)—CH$_2$—CH$_2$—CH$_2$—S—, —N(H)—CH$_2$—CH$_2$—N(H)—CH$_2$—, —N(H)—CH$_2$—CH$_2$—O—CH$_2$—, —N(H)—CH$_2$—CH$_2$—S—CH$_2$—, —N(H)—C(=O)—C(=O)—CH$_2$—, —N(H)—C(=O)—C(=O)—N(H)—, —N(H)—C(=O)—C(=O)—O—, —N(H)—C(=O)—C(=O)—S—, —N(H)—C(=O)—CH$_2$—CH$_2$—, —N(H)—CH$_2$—N(H)—C(=O)—, —CH$_2$—S—CH$_2$—N(H)—, —CH$_2$—N(H)—CH$_2$—S—, —CH$_2$—N(H)—CH$_2$—, —CH$_2$—CH$_2$—N(H)—CH$_2$—, —CH$_2$—CH$_2$—CH$_2$—N(H)—CH$_2$—, —CH$_2$—N(H)—CH$_2$—CH$_2$—O—, or —CH$_2$—N(H)—CH$_2$—CH$_2$—S—.

More specifically, $R_4$ and $R_5$ taken together can be —N(H)—N=N—, —N(H)—$CH_2$—N(H)—, —N(H)—CH=CH—, —N(H)—$CH_2$—$CH_2$—, —N(H)—$CH_2$—$CH_2$—$CH_2$—, —N(H)—$CH_2$—$CH_2$—$CH_2$—$CH_2$—, —N(H)—$CH_2$—$CH_2$—N(H)—, —N(H)—$CH_2$—$CH_2$—O—, —N(H)—$CH_2$—$CH_2$—S—, —N(H)—$CH_2$—$CH_2$—$CH_2$—N(H)—, —N(H)—$CH_2$—$CH_2$—$CH_2$—O—, —N(H)—$CH_2$—$CH_2$—$CH_2$—S—, or —N(H)—C(=O)—C(=O)—N(H)—.

Preferably, $R_4$ and $R_5$ taken together are —N(H)—N=N—, —N(H)—C(=O)—C(=O)—N(H)—, —N(H)—CH=CH—, —N(H)—$CH_2$—$CH_2$—, —N(H)—$CH_2$—$CH_2$—$CH_2$—, or —N(H)—$CH_2$—$CH_2$—N(H)—. More preferably, $R_4$ and $R_5$ taken together are —N(H)—N=N— or —N(H)—C(=O)—C(=O)—N(H)—.

A preferred group of compounds of formula I are compounds wherein $R_1$ and $R_2$ are not both hydrogen.

Another preferred group of compounds of formula I are compounds wherein $R_1$ and $R_2$ are each independently halo (e.g. bromo).

A preferred compound of formula I is a compound of formula III:

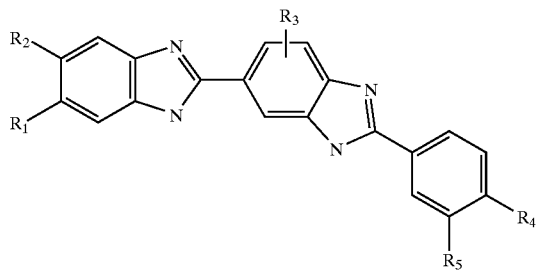

(III)

wherein $R_1$–$R_5$ have any of the values defined herein for a compound of formula I.

Processes for preparing compounds of formula I are illustrated by the following procedures in which the meanings of the generic radicals are as given above unless otherwise qualified.

A compound of formula I wherein $R_4$ and $R_5$ taken together are —N(H)—N=N— can be prepared from a corresponding intermediate of formula II

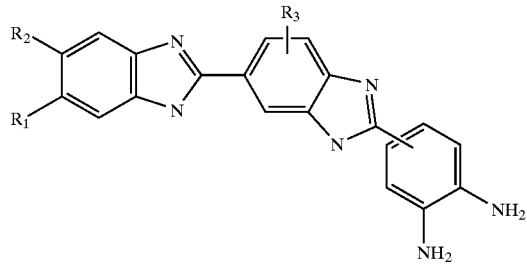

(II)

by treatment with $NaNO_2$ under acidic conditions. Suitable conditions for performing such a transformation are described in Example 1.

A compound of formula I wherein $R_4$ and $R_5$ taken together are —N(H)—C(=O)—C(=O)—N(H)— can be prepared from a corresponding compound of formula II by treatment with oxalic acid under acidic conditions. Suitable conditions for performing such a transformation are described in Example 2.

An intermediate useful for preparing a compound of formula I is an intermediate of formula II.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect topoisomerase I mediated DNA cleavage can be determined using pharmacological models that are well known to the art, for example, using a model like Test A described below.

Test A. Topoisomerase I Cleavage Assay

Representative compounds of the invention were evaluated in a cleavage assay using recombinant topoisomerases I. This assay was preformed as described by B. Gatto et al. *Cancer Res.*, 1996, 56, 2795–2800. Human topoisomerase I was isolated as a recombinant fusion protein using a T7 expression system. Plasmid YEpG was purified by the alkali lysis method followed by phenol deproteination and CsCl/ethidium isopycnic centrifugation as described by Maniatis, T.; Fritsch, E. F.; Sambrook, J. *Molecular Cloning, a Laboratory Manual*; Cold Spring Harbor Laboratory: Cold Spring Harbor, N.Y. 1982; pp 149–185. The end-labeling of the plasmid was accomplished by digestion with a restriction enzyme followed by end-filling with Klenow polymerase as previously described by Liu, L. F.; Rowe, T. C.; Yang, L.; Tewey, K. M.; Chen, G. L. "Cleavage of DNA by mammalian topoisomerase II," *J. Biol. Chem.* 1983, 258, 15365. $IC_{50}$ values were calculated after 4 days of continuous drug exposure. Topoisomerase I cleavage values are reported as REC, Relative Effective Concentration (i.e., concentrations relative to compound 5, whose value is arbitrarily assumed as 1) that is able to produce the same cleavage on the plasmid DNA in the presence of human topoisomerase I.

The cytotoxic effects of a compound of the invention can be determined using pharmacological models that are well known to the art, for example, using a model like Test B described below.

Test B. Cytotoxicity Assay

Cytotoxicity was determined using the MTT-microtiter plate tetrazolinium cytotoxicity assay (MTA) (See Chen A. Y. et al. *Cancer Res.* 1993, 53, 1332; Mosmann, T. J., *J. Immunol. Methods* 1983, 65, 55; and Carmichael, J. et al. *Cancer Res.* 1987, 47, 936). The human lymphoblast RPMI 8402 and its camptothecin-resistant variant cell line, CPT-K5 were provided by Dr. Toshiwo Andoh (Aichi Cancer Center Research Institute, Nagoya, Japan) (see Andoh, T.; Okada, K. "Drug resistance mechanisms of topoisomerase I drugs," *Adv. in Pharmacology* 1994, 29B, 93. The cytotoxicity assay was performed using 96-well microtiter plates. Cells were grown in suspension at 37° C. in 5% $CO_2$ and maintained by regular passage in RPMI medium supplemented with 10% heat-inactivated fetal bovine serum, L-glutamine (2 mM), penicillin (100 U/mL), and streptomycin (0.1 mg/mL). For determination of $IC_{50}$, cells were exposed continuously with varying concentrations of drug and MTT assays were performed at the end of the fourth day.

Data from Test A and Test B is shown in Table 1 for representative compounds of the invention.

TABLE 1

Pharmacological Activity of Compounds of the Invention

| Compound | Topo I-mediated DNA cleavage[b] | Cytotoxicity $IC_{50}$ ($\mu M$) | |
|---|---|---|---|
| | | RPMI | CPT-K5 |
| 5 | 1 | 0.09 | 0.70 |
| 2 | 1 | 0.47 | 0.47 |
| 3 | 1 | 2.3 | 21 |
| 4 | — | 20 | >20 |

Compounds of formula I are potent topoisomerase I poisons. Additionally, compounds of formula I exhibit cytotoxic activity against RPMI 8402 cancer cells and camptothecin resistant CPT-K5 cells. Accordingly, compounds of formula I are useful as cytotoxic agents, for the treatment of cancers, and in particular, solid mammalian tumors or hematologic malignancies. Compounds of the invention are also useful as pharmacological tools for in vitro and in vivo study of topoisomerase function and activity.

Comparison of the data for compounds 2 and 3 with the data for compound 4 suggests that topoisomerase poisoning activity and cytotoxic activity improve when $R_4$ and $R_5$ taken together are a chain comprising a H-bonding functionality (e.g. N—H). Thus, the invention provides compounds of formula I wherein $R_4$ and $R_5$ taken together are a chain that comprises at least one N—H group.

As used herein, the term "solid mammalian tumors" includes cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

The invention will now be illustrated by the following non-limiting Examples, wherein unless otherwise stated: melting points were determined with a Thomas-Hoover Unimelt capillary melting point apparatus; column chromatography refers to flash chromatography conducted on SiliTech 32–63 $\mu$m, (ICN Biomedicals, Eschwegge, Ger.) using the solvent systems indicated; infrared spectral data (IR) were obtained on a Perkin-Elmer 1600 Fourier transform spectrophotometer and are reported in $cm^{-1}$; proton ($^1H$ NMR) and carbon ($^{13}C$ NMR) nuclear magnetic resonance were recorded on a Varian Gemini-200 Fourier Transform spectrometer; NMR spectra (200 MHZ $^1H$ and 50 MHZ $^{13}C$) were recorded in the deuterated solvent indicated with chemical shifts reported in $\delta$ units downfield from tetramethylsilane (TMS); coupling constants are reported in hertz (Hz); mass spectra were obtained from Washington University Resource for Biomedical and Bio-organic Mass Spectrometry within the Department of Chemistry at Washington University, St. Louis, Mo.; and combustion analyses were performed by Atlantic Microlabs, Inc., Norcross, Ga., and were within ±0.4% of the theoretical value.

EXAMPLES

Example 1

5-Phenyl-2'-(benzotriazol-5-yl)-bibenzimidazole (2)

5-Phenyl-2-[2'-(3,4-aminophenyl)benzimidazol-5'yl]benzimidazole (1), (58 mg, 0.14 mmol) was dissolved in 0.1N HCl. This solution was placed in an ice bath and while maintaining a reaction temperature below 10° C. $NaNO_2$ (10.2 mg) in 5 mL water was added dropwise. The reaction mixture was stirred for 15 minutes, neutralized with 0.1N KOH, extracted with ethyl acetate, and the resulting material was purified by chromatography, with 10% methanol:ethyl acetate as the eluent to give the title compound as a dark brown solid which had to be immediately stored in an amber vial because of its light sensitivity; 42 mg (71%); mp>280° C.; IR (KBr) 3385, 3128, 3056, 1626, 1431, 1287; UV (MeOH) 340, 245, 230 nm (log $\in$=4.59, 4.59, 4.59); $^1H$ NMR (DMSO-$d_6$+3 drops of $CF_3COOH$) $\delta$ 7.47–7.61 (m, 3H), 7.79–8.07 (m, 6H), 8.15–8.19 (m, 2H), 8.40 (d, 1H, J=9.0), 8.63 (s, 1H), 8.67 (s, 1H); $^{13}C$ NMR (DMSO-$d_6$+3 drops of $CF_3COOH$) $\delta$ 107.4, 111.7, 114.1, 114.6, 115.9, 116.3, 117.8, 122.3, 123.2, 125.5, 125.6, 126.6, 128.0, 129.2, 129.5, 131.9, 133.2, 134.7, 138.7, 139.8, 141.4, 147.1, 150.7, 154.3; HRMS (FAB) calcd for $C_{26}H_{17}N_7$ (MH$^+$) 428.1624, found 428.1622.

The intermediate 5-Phenyl-2-[2'-(3,4-aminophenyl)benzimidazol-5'yl]benzimidazole was prepared as follows.

a. 5-Phenyl-2-[2'-(3,4-aminophenyl)benzimidazol-5'yl]benzimidazole.

A solution of 5-phenyl-2-[2'-(3,4-dinitrophenyl)benzimidazol-5'yl]benzimidazole (75 mg, 0.16 mmol) in ethyl acetate (50 mL) was reduced by hydrogenation over 10% Pd/C (15 mg) for 90 minutes. The resulting solution was passed through a bed of Celite and the ethyl acetate was removed to give the diamine 1, which was used without further purification.

The starting 5-phenyl-2-[2'-(3,4-dinitrophenyl)benzimidazol-5'yl]benz-imidazole can be prepared as described by J. S. Kim et al. *J. Med. Chem.* 1997, 40, 2818–2824.

Example 2

5-Phenyl-2'-(quinoxaline-6-yl)-bibenzimidazole (3)

Diamine 1 (55 mg, 0.13 mmol) was dissolved in water (4 mL) and heated to 70° C. Glyoxal 2NaHSO$_3$ (50 mg, 0.13 mmol) was dissolved in hot water (80° C., 3 mL) and added to the diamine slowly (as described by Jones, R. G.; McLaughlin, K. C. 2,3-Pyrazinedicarboxylic acid. *Org. synth.* 1950, 30, 86). After 15 minutes, the reaction mixture was cooled to room temperature and Na$_2$CO$_3$ was added. Extraction with ether followed by chromatographic separation with 10% methanol:ethyl acetate as the eluent gave the title compound as a yellow solid; 38 mg (67%); mp 235° C.; IR (KBr) 3385, 3169, 1624, 1554, 1431, 1297; UV (MeOH) 360, 255, 220 nm (log $\in$=4.52, 4.65, 4.59); $^1$H NMR (DMSO-d$_6$+3 drops of CF$_3$COOH) δ 7.46–7.61 (m, 3H), 7.80 (d, 2H, J=8.0), 7.89–8.26 (m, 5H), 8.36 (d, 1H, J=9.0), 8.69–8.78 (m, 2H), 9.04–9.10 (m, 3H); $^{13}$C NMR (DMSO-d$_6$+3 drops of CF$_3$COOH) δ 111.7, 114.6, 116.5, 116.6, 117.9, 123.5, 123.9, 125.6, 127.5, 128.1, 128.2, 128.3, 128.6, 130.6, 131.6, 132.9, 138.9, 139.1, 139.7, 142.5, 143.7, 143.8, 147.3, 150.5, 153.1; HRMS (FAB) calcd for $C_{28}H_{19}N_6$ (MH$^+$) 439.1671, found 439.1677.

Example 3

5-Phenyl-2'-(quinoxalinedione-6-yl)bibenzimidazole (4)

Diamine 1 (40 mg, 0.096 mmol) and oxalic acid (20 mg, 0.22 mmol) in 4 N HCl were refluxed overnight (as described by Ohmori, J. Et al. *J. Med. Chem.* 1996, 39, 1331–1338). Upon standing at room temperature, the title compound precipitated from the reaction mixture as a brownish solid; 15 mg (33%); mp>280° C.; IR (KBr) 3339, 3217, 2845, 1623, 1578, 1506, 1469, 1272; $^1$H NMR (DMSO-d$_6$) δ 6.96 (d, 1H, J=9.0), 7.41–7.60 (m, 4H), 7.77–8.00 (m, 7H), 8.32 (d, 1H, J=9.0), 8.57 (s, 1H); $^{13}$C NMR (DMSO-d$_6$+3 drops of CF$_3$COOH) δ 106.5, 107.4, 111.7, 114.1, 114.7, 115.2, 116.7, 119.5, 122.3, 124.7, 125.7, 127.5, 128.2, 129.4, 131.9, 133.2, 138.8, 139.7, 139.8, 149.7, 152.7, 158.2; HRMS (FAB) calcd for $C_{28}H_{19}N_6O_2$ (MH$^+$) 471.1569, found 471.1584.

Example 4

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution | |
| (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution | |
| (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

The invention has been described with reference to various specific and preferred embodiments and techniques. However, it should be understood that many variations and modifications may be made while remaining within the spirit and scope of the invention.

What is claimed is:

1. A therapeutic method comprising inhibiting cancer cells by administering to a mammal in need of such therapy, an amount of a compound of formula I:

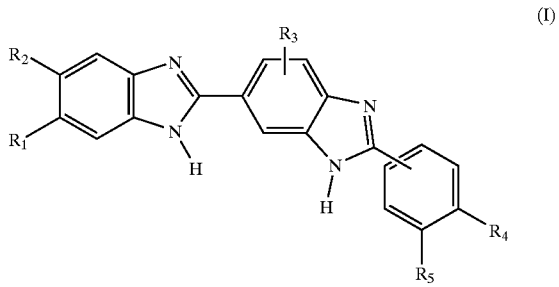

wherein:
$R_1$ and $R_2$ are each independently hydrogen, $(C_1-C_6)$alkyl, $(C_3-C_6)$cycloalkyl, $(C_1-C_6)$alkoxy, nitro, hydroxyl, halo$(C_1-C_6)$alkyl, trifluoromethoxy, halo, $(C_3-C_6)$cycloalkyl$(C_1-C_6)$alkyl, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, aryl or heteroaryl; or $R_1$ and $R_2$ taken together are methylenedioxy; or $R_1$ and $R_2$ taken together with the atoms to which they are attached are benzo; wherein any aryl, heteroaryl, or benzo may optionally be substituted by 1, 2, or 3 substituents independently selected from the group consisting of $(C_1-C_6)$alkyl, $(C_3-C_6)$cycloalkyl, $(C_1-C_6)$alkoxy, nitro, hydroxyl, halo$(C_1-C_6)$alkyl, trifluoromethoxy, $(C_3-C_6)$cycloalkyl$(C_1-C_6)$alkyl, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, and halo;

$R_3$ is hydrogen, $(C_1-C_6)$alkyl, $(C_3-C_6)$cycloalkyl, $(C_1-C_6)$alkoxy, nitro, hydroxyl, halo$(C_1-C_6)$alkyl, trifluoromethoxy, $(C_3-C_6)$cycloalkyl$(C_1-C_6)$alkyl, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, or halo; and $R_4$ and $R_5$ taken together are a 3, 4, or 5 membered saturated or unsaturated chain comprising members selected from the group consisting of non-peroxide oxygen, sulfur, N(X), and carbon, optionally substituted by oxo; wherein each X is independently absent or is H, O, $(C_1-C_6)$alkyl, phenyl or benzyl; and wherein at least one of said chain members is an N—H group; or a pharmaceutically acceptable salt thereof;

provided $R_4$ and $R_5$ taken together are not —N(H)—C(H)=N—; and provided $R_4$ and $R_5$ taken together are not —N(H)—C(H)=N— substituted by oxo;

effective to inhibit said cancer cells.

2. The method of claim 1 wherein $R_1$ is hydrogen, halo, aryl or heteroaryl; wherein any aryl or heteroaryl may optionally be substituted by 1, 2, or 3 substituents independently selected from the group consisting of $(C_1-C_6)$alkyl, $(C_3-C_6)$cycloalkyl, $(C_1-C_6)$alkoxy, nitro, hydroxyl, halo$(C_1-C_6)$alkyl, trifluoromethoxy, and halo.

3. The method of claim 1 wherein $R_2$ is hydrogen, halo, aryl or heteroaryl; wherein any aryl or heteroaryl may optionally be substituted by 1, 2, or 3 substituents independently selected from the group consisting of $(C_1-C_6)$alkyl, $(C_3-C_6)$cycloalkyl, $(C_1-C_6)$alkoxy, nitro, hydroxyl, halo $(C_1-C_6)$alkyl, trifluoromethoxy, $(C_3-C_6)$cycloalkyl$(C_1-C_6)$alkyl, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, and halo.

4. The method of claim 1 wherein $R_1$ and $R_2$ taken together are methylenedioxy.

5. The method of claim 1 wherein $R_1$ and $R_2$ taken together are benzo, which benzo is optionally substituted by 1, 2, or 3 substituents independently selected from the group consisting of $(C_1-C_6)$alkyl, $(C_3-C_6)$cycloalkyl, $(C_1-C_6)$alkoxy, nitro, hydroxyl, halo$(C_1-C_6)$alkyl, trifluoromethoxy, $(C_3-C_6)$cycloalkyl$(C_1-C_6)$alkyl, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, and halo.

6. The method of claim 1 wherein $R_3$ is hydrogen.

7. The method of claim 1 wherein $R_3$ is $(C_1-C_6)$alkoxy, nitro, hydroxyl, halo$(C_1-C_6)$alkyl, trifluoromethoxy, $(C_1-C_6)$alkanoyl, hydroxy$(C_1-C_6)$alkyl, $(C_1-C_6)$alkoxycarbonyl, $(C_1-C_6)$alkylthio, $(C_2-C_6)$alkanoyloxy, or halo.

8. The method of claim 1 wherein $R_4$ and $R_5$ taken together are —N(H)—N=N—, —N(H)—N(H)—CH$_2$—, —N(H)—N(H)—CH$_2$—CH$_2$—, —N(H)—CH$_2$—N(H)—, —N(H)—CH=CH—, —N(H)—CH$_2$—CH$_2$—, —N(H)—CH$_2$—CH$_2$—CH$_2$—, —N(H)—CH$_2$—CH$_2$—CH$_2$—CH$_2$—, —N(H)—CH$_2$—CH$_2$—N(H)—, —N(H)—CH$_2$—CH$_2$—O—, —N(H)—CH$_2$—CH$_2$—S—, —N(H)—CH$_2$—CH$_2$—CH$_2$—N(H)—, N(H)—CH$_2$—CH$_2$—CH$_2$—O—, —N(H)—CH$_2$—CH$_2$—CH$_2$—S—, —N(H)—CH$_2$—CH$_2$—N(H)—CH$_2$—, —N(H)—CH$_2$—CH$_2$—O—CH$_2$—, —N(H)—CH$_2$—CH$_2$—S—CH$_2$—, —N(H)—C(=O)—C(=O)—CH$_2$—, —N(H)—C(=O)—C(=O)—N(H)—, —N(H)—C(=O)—C(=O)—O—, —N(H)—C(=O)—C(=O)—S—, —N(H)—C(=O)—CH$_2$—CH$_2$—, —N(H)—CH$_2$—N(H)—C(=O)—, —CH$_2$—S—CH$_2$—N(H)—, —CH$_2$—N(H)—CH$_2$—S—, —CH$_2$—N(H)—CH$_2$—, —CH$_2$—CH$_2$—N(H)—CH$_2$—, —CH$_2$—CH$_2$—CH$_2$—N(H)—CH$_2$—, —CH$_2$—N(H)—CH$_2$—CH$_2$—O—, or —CH$_2$—N(H)—CH$_2$—CH$_2$—S—.

9. The method of claim 1 wherein $R_4$ and $R_5$ taken together are —N(H)—N=N—, —N(H)—CH$_2$—N(H)—, —N(H)—CH=CH—, —N(H)—CH$_2$—CH$_2$—, —N(H)—CH$_2$—CH$_2$—CH$_2$—, —N(H)—CH$_2$—CH$_2$—CH$_2$—CH$_2$—, —N(H)—CH$_2$—CH$_2$—N(H)—, —N(H)—CH$_2$—CH$_2$—O—, —N(H)—CH$_2$—CH$_2$—S—, —N(H)—CH$_2$—CH$_2$—CH$_2$—N(H)—, —N(H)—CH$_2$—CH$_2$—CH$_2$—O—, —N(H)—CH$_2$—CH$_2$—CH$_2$—S—, or —N(H)—C(=O)—C(=O)—N(H)—.

10. The method of claim 1 wherein $R_4$ and $R_5$ taken together are —N(H)—N=N—, —N(H)—C(=O)—C(=O)—N(H)—, —N(H)—CH=CH—, —N(H)—CH$_2$—CH$_2$—, —N(H)—CH$_2$—CH$_2$—CH$_2$—, or —N(H)—CH$_2$—CH$_2$—N(H)—.

11. The method of claim 1 wherein $R_4$ and $R_5$ taken together are —N(H)—N=N— or —N(H)—C(=O)—C(=O)—N(H)—.

12. The method of claim 1 wherein $R_1$ and $R_2$ are not both hydrogen.

13. The method of claim 1 wherein $R_1$ and $R_2$ are each independently halo.

14. The method of claim 1 wherein $R_1$ and $R_2$ are each bromo.

15. A method comprising inhibiting cancer cells by contacting said cancer cells with an effective amount of a compound of formula I:

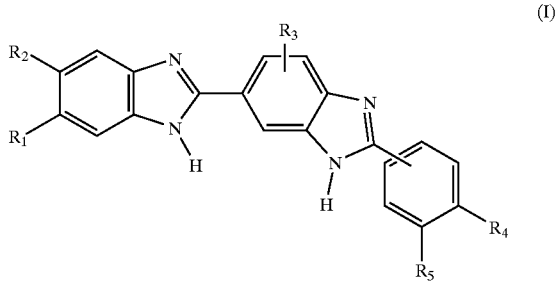

wherein:
R$_1$ and R$_2$ are each independently hydrogen, (C$_1$–C$_6$) alkyl, (C$_3$–C$_6$)cycloalkyl, (C$_1$–C$_6$)alkoxy, nitro, hydroxyl, halo(C$_1$–C$_6$)alkyl, trifluoromethoxy, halo, (C$_3$–C$_6$)cycloalkyl(C$_1$–C$_6$)alkyl, (C$_1$–C$_6$)alkanoyl, hydroxy(C$_1$–C$_6$)alkyl, (C$_1$–C$_6$)alkoxycarbonyl, (C$_1$–C$_6$)alkylthio, (C$_2$–C$_6$)alkanoyloxy, aryl or heteroaryl; or R$_1$ and R$_2$ taken together are methylenedioxy; or R$_1$ and R$_2$ taken together with the atoms to which they are attached are benzo; wherein any aryl, heteroaryl, or benzo may optionally be substituted by 1, 2, or 3 substituents independently selected from the group consisting of (C$_1$–C$_6$)alkyl, (C$_3$–C$_6$)cycloalkyl, (C$_1$–C$_6$)alkoxy, nitro, hydroxyl, halo(C$_1$–C$_6$)alkyl, trifluoromethoxy, (C$_3$–C$_6$)cycloalkyl(C$_1$–C$_6$)alkyl, (C$_1$–C$_6$)alkanoyl, hydroxy(C$_1$–C$_6$)alkyl, (C$_1$–C$_6$) alkoxycarbonyl, (C$_1$–C$_6$)alkylthio, (C$_2$–C$_6$)alkanoyloxy, and halo;

R$_3$ is hydrogen, (C$_1$–C$_6$)alkyl, (C$_3$–C$_6$)cycloalkyl, (C$_1$–C$_6$)alkoxy, nitro, hydroxy, halo(C$_1$–C$_6$)alkyl, trifluoromethoxy, (C$_3$–C$_6$)cycloalkyl(C$_1$–C$_6$)alkyl, (C$_1$–C$_6$)alkanoyl, hydroxy(C$_1$–C$_6$)alkyl, (C$_1$–C$_6$) alkoxycarbonyl, (C$_1$–C$_6$)alkylthio, (C$_2$–C$_6$)alkanoyloxy, or halo; and R$_4$ and R$_5$ taken together are a 3, 4, or 5 membered saturated or unsaturated chain comprising members selected from the group consisting of non-peroxide oxygen, sulfur, N(X), and carbon, optionally substituted by oxo; wherein each X is independently absent or is H, O, (C$_1$–C$_6$)alkyl, phenyl or benzyl; and wherein at least one of said chain members is an N—H group; or a pharmaceutically acceptable salt thereof;

provided R$_4$ and R$_5$ taken together are not —N(H)—C (H)=N—; and provided R$_4$ and R$_5$ taken together are not —N(H)—C(H)=N— substituted by oxo.

16. The method of claim 15 wherein R$_1$ is hydrogen, halo, aryl or heteroaryl; wherein any aryl or heteroaryl may optionally be substituted by 1, 2, or 3 substituents independently selected from the group consisting of (C$_1$–C$_6$)alkyl, (C$_3$–C$_6$)cycloalkyl, (C$_1$–C$_6$)alkoxy, nitro, hydroxy, halo (C$_1$–C$_6$)alkyl, trifluoromethoxy, and halo.

17. The method of claim 15 wherein R$_2$ is hydrogen, halo, aryl or heteroaryl; wherein any aryl or heteroaryl may optionally be substituted by 1, 2, or 3 substituents independently selected from the group consisting of (C$_1$–C$_6$)alkyl, (C$_3$–C$_6$)cycloalkyl, (C$_1$–C$_6$)alkoxy, nitro, hydroxyl, halo (C$_1$–C$_6$)alkyl, trifluoromethoxy, (C$_3$–C$_6$)cycloalkyl(C$_1$–C$_6$) alkyl, (C$_1$–C$_6$)alkanoyl, hydroxy(C$_1$–C$_6$)alkyl, (C$_1$–C$_6$) alkoxycarbonyl, (C$_1$–C$_6$)alkylthio, (C$_2$–C$_6$)alkanoyloxy, and halo.

18. The method of claim 15 wherein R$_1$ and R$_2$ taken together are methylenedioxy.

19. The method of claim 15 wherein R$_1$ and R$_2$ taken together are benzo, which benzo is optionally substituted by 1, 2, or 3 substituents independently selected from the group consisting of (C$_1$–C$_6$)alkyl, (C$_3$–C$_6$)cycloalkyl, (C$_1$–C$_6$) alkoxy, nitro, hydroxyl, halo(C$_1$–C$_6$)alkyl, trifluoromethoxy, (C$_3$–C$_6$)cycloalkyl(C$_1$–C$_6$)alkyl, (C$_1$–C$_6$)alkanoyl, hydroxy (C$_1$–C$_6$)alkyl, (C$_1$–C$_6$)alkoxycarbonyl, (C$_1$–C$_6$)alkylthio, (C$_2$–C$_6$)alkanoyloxy, and halo.

20. The method of claim 15 wherein R$_3$ is hydrogen.

21. The method of claim 15 wherein R$_3$ is (C$_1$–C$_6$)alkoxy, nitro, hydroxy, halo(C$_1$–C$_6$)alkyl, trifluoromethoxy, (C$_1$–C$_6$) alkanoyl, hydroxy(C$_1$–C$_6$)alkyl, (C$_1$–C$_6$)alkoxycarbonyl, (C$_1$–C$_6$)alkylthio, (C$_2$–C$_6$)alkanoyloxy, or halo.

22. The method of claim 15 wherein R$_4$ and R$_5$ taken together are —N(H)—N=N—, —N(H)—N(H)—CH$_2$—, —N(H)—N(H)—CH$_2$—CH$_2$—, —N(H)—CH$_2$—N(H)—, —N(H)—CH=CH—, —N(H)—CH$_2$—CH$_2$—, —N(H)—CH$_2$—CH$_2$—CH$_2$—, —N(H)—CH$_2$—CH$_2$—CH$_2$—CH$_2$—, —N(H)—CH$_2$—CH$_2$—N (H)—, —N(H)—CH$_2$—CH$_2$—O—, —N(H)—CH$_2$—CH$_2$—S—, —N(H)—CH$_2$—CH$_2$—CH$_2$—N (H)—, —N(H)—CH$_2$—CH$_2$—CH$_2$—O—, —N(H)—CH$_2$—CH$_2$—CH$_2$—S—, —N(H)—CH$_2$—CH$_2$—N(H)—CH$_2$—, —N(H)—CH$_2$—CH$_2$—O—CH$_2$—, —N(H)—CH$_2$—CH$_2$—S—CH$_2$—, —N(H)—C(=O)—C(=O)—CH$_2$—, —N(H)—C(=O)—C(=O)—N(H)—, —N(H)—C(=O)—C(=O)—O—, —N(H)—C(=O)—C(=O)—S—, —N(H)—C(=O)—CH$_2$—CH$_2$—, —N(H)—CH$_2$—N(H)—C(=O)—, —CH$_2$—S—CH$_2$—N(H)—, —CH$_2$—N(H)—CH$_2$—S—, —CH$_2$—N(H)—CH$_2$—, —CH$_2$—CH$_2$—N(H)—CH$_2$—, —CH$_2$—CH$_2$—CH$_2$—N (H)—CH$_2$—, —CH$_2$—N(H)—CH$_2$—CH$_2$—O—, or —CH$_2$—N(H)—CH$_2$—CH$_2$—S—.

23. The method of claim 15 wherein R$_4$ and R$_5$ taken together are —N(H)—N=N—, —N(H)—CH$_2$—N(H)—, —N(H)—CH=CH—, —N(H)—CH$_2$—CH$_2$—, —N(H)—CH$_2$—CH$_2$—CH$_2$—, —N(H)—CH$_2$—CH$_2$—CH$_2$—CH$_2$—, —N(H)—CH$_2$—CH$_2$—N (H)—, —N(H)—CH$_2$—CH$_2$—O—, —N(H)—CH$_2$—CH$_2$—S—, —N(H)—CH$_2$—CH$_2$—CH$_2$—N (H)—, —N(H)—CH$_2$—CH$_2$—CH$_2$—O—, —N(H)—CH$_2$—CH$_2$—CH$_2$—S—, or —N(H)—C(=O)—C(=O)—N(H)—.

24. The method of claim 15 wherein R$_4$ and R$_5$ taken together are —N(H)—N=N—, —N(H)—C(=O)—C (=O)—N(H)—, —N(H)—CH=CH—, —N(H)—CH$_2$—CH$_2$—, —N(H)—CH$_2$—CH$_2$—CH$_2$—, or —N(H)—CH$_2$—CH$_2$—N(H)—.

25. The method of claim 15 wherein R$_4$ and R$_5$ taken together are —N(H)—N=N— or —N(H)—C(=O)—C (=O)—N(H)—.

26. The method of claim 15 wherein R$_1$ and R$_2$ are not both hydrogen.

27. The method of claim 15 wherein R$_1$ and R$_2$ are each independently halo.

28. The method of claim 15 wherein R$_1$ and R$_2$ are each bromo.

* * * * *